(12) United States Patent
Mertens

(10) Patent No.: US 7,189,383 B2
(45) Date of Patent: Mar. 13, 2007

(54) RADIOACTIVELY LABELLED AMINO ACID ANALOGUES, THEIR PREPARATION AND USE

(75) Inventor: John J. R. Mertens, Vilvoorde (BE)

(73) Assignee: Mallinckrodt Inc., St. Louis ( * ) Notice: Subject to any disclaimer, the term of this patent is extended or adjusted under 35 U.S.C. 154(b) by 60 days.

(21) Appl. No.: 10/523,184

(22) PCT Filed: Aug. 1, 2003

(86) PCT No.: PCT/US03/24436

§ 371 (c)(1),
(2), (4) Date: Jan. 28, 2005

(87) PCT Pub. No.: WO2004/110500

PCT Pub. Date: Dec. 23, 2004

(65) Prior Publication Data

US 2006/0127306 A1    Jun. 15, 2006

(30) Foreign Application Priority Data

Aug. 2, 2002    (EP)    ................................ 02078228

(51) Int. Cl.
A61K 49/06    (2006.01)
A01N 43/40    (2006.01)
C07D 221/00    (2006.01)

(52) U.S. Cl. ..................... 424/9.4; 424/9.44; 424/9.45; 514/345; 514/358; 546/290; 546/300; 546/329; 546/346

(58) Field of Classification Search ................. 424/9.4; 514/345, 358; 546/300, 329, 346
See application file for complete search history.

(56) References Cited

FOREIGN PATENT DOCUMENTS

| EP | 0 451 422 A1 | 10/1991 |
|---|---|---|
| GB | 1220591 A | 1/1971 |
| GB | 2020275 A | 11/1979 |
| WO | WO 03/099746 A1 | 12/2003 |

OTHER PUBLICATIONS

Tetrahedron, Sheffer-Dee-Noor et al. 1994, 50(23), 7009-18.*
Deehan, B et.al. "Uptake and Distribution of L-3-I-125 Lodo-alpha-methyl tyrosine in exp. rat . . . " Euro.J.of Nuc. Med., Feb. 1993, p. 101-106,vol. 20, No. 2, Berlin, DE.
Wester H.J. et.al. "Synth. and Radi. of O-('18F!fluorethyl)-L-tyrosine for tum. imag.", J. of Nuc. Med.: Off. Publ., Soc. of Nuc.Med.,Jan. 1999,pp. 205-212, vol. 40,No. 1.
Ishiwata K. et.al.:"Synth. and Rad. Dos. of 4-Borono-2-(18F)Fluoro . . . ", Intl. Jnl. of Rad., Jun. 25, 1990, pp. 325-328, vol. 42, No. 2, Pergamon PressLTD, GB.
Kawai K et. al."Monoiodo-D-Tyrosine, an artif. Amino Acid . . . ", Nuc. Med. and Bio., 1990, pp. 369-376, vol. 17, No. 4, Pergamon, Oxford, GB.
Bergstrom, et.al."PET study of methionine accum. in glioma . . . ", Jnl of Comp. Assist. Tomography, 1987,pp. 208-213, vol. 11, No. 2,Raven Press, NY.
Coenen, et.al."Cerebral metabolism of L-2-18F- . . . ", J. Nucl. Med., Aug. 1989, pp. 1367-1372, vol. 30,No. 8.
Biersack, et. al."Imaging of brain tumors with L-3-[123I]-iodo . . . ", J. Nucl. Med., 1989, pp. 110-112, vol. 30.
Jager, P.L.et.al.,"Uptake mechanism of L-3-[125I]iodo-alpha-methyl- . . . "Nuc. Med. Comm., 2001,pp. 87-96,vol. 22, No. 1, Lippincott Williams & Wilkins.
Lahoutte, et.al."In vitro charac. of the influx of 3-[125I]iodo- . . . ", Nuc. Med. of Bio., 2001,pp. 129-134, vol. 28,Elsevier Science Inc.
Heiss, et.al."Invest. of transport mech. and uptake kinetics of O-2-[18f]fluoroethyl)-L- . . . ", J. Nuc. Med., 1999,pp. 1367-1373, vol. 40.
Vekeman, et.al.,"L-[2-radioiodo]Tyrosine, a new potential protein synthesis . . . ",Eur. J. Nuc. Med., 1999, pp. 971, vol. 26, No. 9.
Mertens, et.al."Uptake study of L-2-I251-o-Tyrosine, . . . "Eur. J. Nuc. Med.,2000, p. 1063, vol. 27.
Mertens, et.al."New approach of cell uptake kinetics of L-2-123I-Tyr . . . ", Eur. J. Nuc. Med. Mol. Imag., 2002, p. S377-P722, vol. 29.
Samnick, et.al."Initial evaluation on the feasibility of SPECT with p-iodo-Lphenylalanine . . . ", Nuc. Med. Com., 2002, pp. 121-130, vol. 23, No. 2, Lippincott Williams & Wilkins.
Rau, et.al."O-(2-[(18)F]Fluoroethyl)-L-tyrosine (FET):a tracer for differentiation . . . ", Eur. J. Nuc. Med. Mol. Imag., 2002, pp. 1039-1046, vol. 29, No. 8, Springer-Verlag.
Wester, et.al."Synthesis and Radiopharm.of 0-(2-[18F]fluoroethyl)-L . . . ", J. Nucl. Med., 1999, pp. 205-212, vol. 40.
Mertens, et.al."Synthesis, radiosynthesis and in vitro charac . . . ", Nuc. Med. Bio., 2004, pp. 739-746, vol. 31, Elsevier Inc.
Mertens,et.al."L-[2-Radioiodo]-Tyrosine a potential tumour tracer for SPECT . . . ",J. of Label.Comp. and Radiopharm.,May 2001,pp. S860-S862,vol. 44(Suppl. 1).
Hamacher, et.al."Efficient rountine production of the 18F-labelled . . . ", Applied Rad. and Isotopes, 2002, pp. 853-856, vol. 40(issue 6), Elsevier Science, Ltd.
Hamacher, et.al."Convenient synth. of n.c.a. O-(2-[18F]Fluoroethyl)- . . . ", J. Labelled Cpd. Radiopharm., 2001, p. S855, vol. 44.
Lahoutte, et.al."Comparative Biodistrib. of Iodinated Amino Acids in Rats . . . ",Biodistrib.of Iodinated Aminos Acids, 2003, pp. 1489-1494, vol. 44, No. 9.

* cited by examiner

Primary Examiner—Kamal A. Saeed
Assistant Examiner—Yong Chu

(57) ABSTRACT

The present invention relates to Halogenated amino acid analogues for use in diagnosis, which compounds have the general formula (I) wherein: R is $(C_1-C_6)$ alkyl optionally substituted with thioether or ether oxygen atom when n=0, or a substituted aromatic or heteraromatic ring when n=1–6; and m=0 or 1; and X is a halogen atom. The invention further relates to precursor compounds for these analogues, to a method of preparing these analogues, to a pharmaceutical composition comprising these analogues and to the use of these analogues and compositions in the diagnosis of cancer

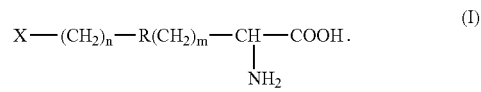

10 Claims, 2 Drawing Sheets

RADIOACTIVELY LABELLED AMINO ACID ANALOGUES, THEIR PREPARATION AND USE

CROSS-REFERENCE TO RELATED APPLICATIONS

Figure 1:
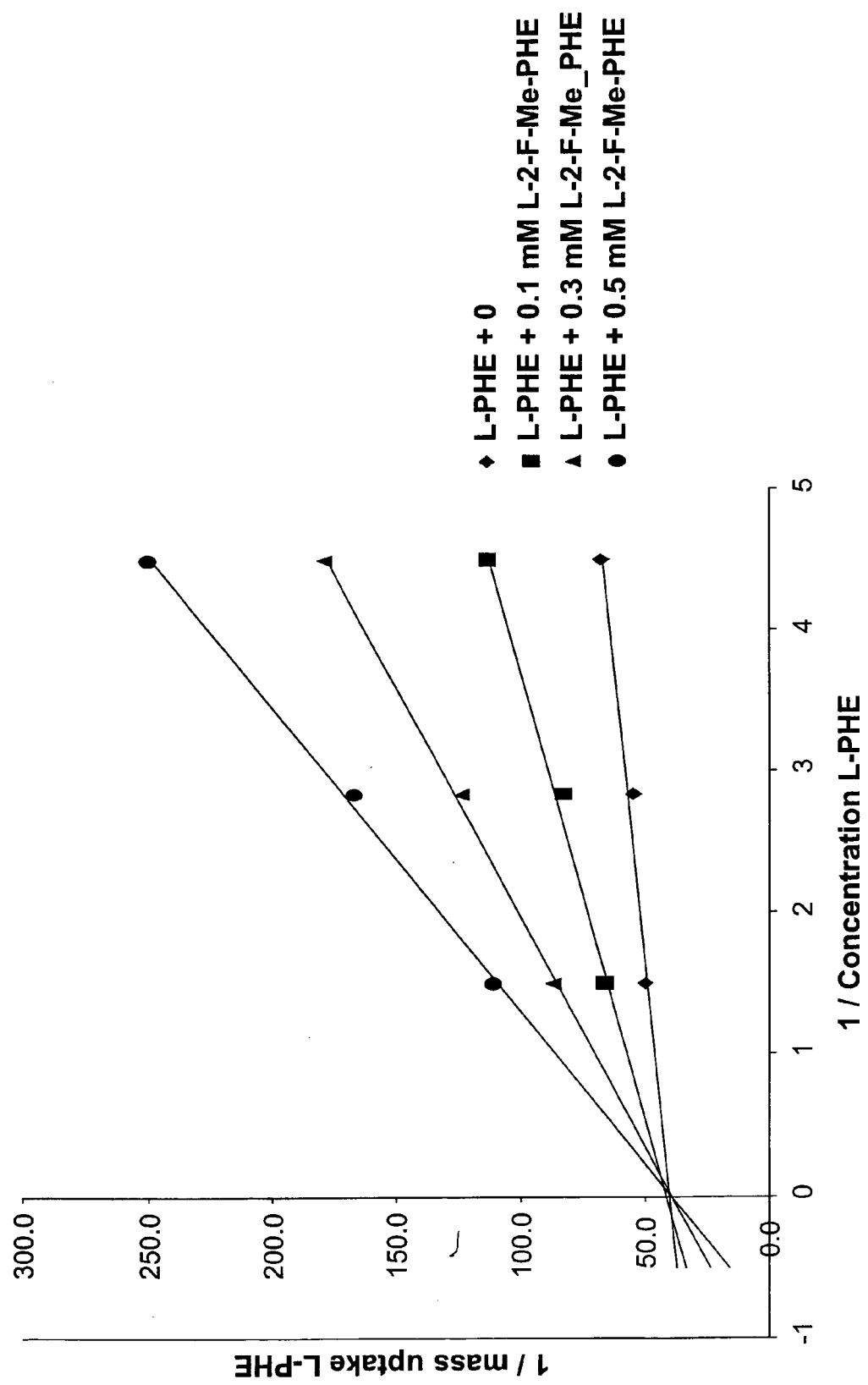

This application claims priority from PCT International Publication Number WO 2004/110500 filed Aug. 1, 2003 and from EPO Patent Application Number 02078228.0 filed Aug. 2, 2002.

FIELD OF THE INVENTION

The present invention relates to amino acid analogues labelled with halogen atom, such as a radioactive fluorine atom, such as F-18, or a non-radioactive fluorine atom, such as F-19. The invention further relates to precursor compounds for and a method of preparing these analogues, to a pharmaceutical composition comprising these analogues and to the use of this composition for diagnosis, for example by means of Positron Emission Tomography or functional MRI.

BACKGROUND OF THE INVENTION

Whatever the new approaches for therapy of cancers will be in the future, an accurate and specific non-invasive diagnosis on bio-molecular level of tumours and metastases will remain of primary importance. Transformation of normal cells into malignant cells is caused by changes in the genetic material, resulting in subtle but fundamental metabolic changes like increased glucose metabolism and increased amino acid uptake and metabolism. These changes in the metabolic phenotype permit the in-vivo study of tumours using radioactive labelled tracers coupled to SPECT (Single Photon Emission Computed Tomography) or PET (Positron Emission Tomography). PET linked coincidence acquisition allows a better resolution and quantification than SPECT, needed for tumour tracing and dimensioning.

Currently, the use of $^{18}$F-FDG (fluoro-deoxyglucose) and PET is the most important technique in nuclear medicine for the study of oncology patients. Although this method is very sensitive, it has two major limitations, namely an avid accumulation in inflammatory lesions and high uptake in the brain, jeopardizing the diagnosis of brain tumours.

It was shown that the use of radioactive amino acids for SPECT and PET could overcome these shortcomings for the larger part. In the late 80's, several $^{11}$C-labelled amino acids like methionine and tyrosine, as well as 2-$^{18}$F-tyrosine (2-$^{18}$F-Tyr) of high specific activity were used for PET studies. At that time it was believed that a high specific activity was required and that for tumour-specification the labelled amino acid had to be involved in a high rate protein incorporation. None of these amino acids has meanwhile been introduced into routine clinical PET because of the short half life and insufficient in vivo stability of C-11 or complicated radiochemical synthesis resulting in insufficient yield (such as for 2-$^{18}$F-Tyr).

About the same time, L-3-$^{123}$I-alpha-methyl-tyrosine (3-$^{123}$I-IMT) was introduced as a SPECT tracer for brain tumours and is used until now also for other tumours like sarcoma and lymphoma. The uptake of this tracer in tumours occurs for the larger part by the L transport system. The plasma membrane transport system L is in many cells the only (efficient) pathway for the import of large branched and aromatic neutral amino acids. The L-type amino acid transporter 1 (LAT1) is a Na$^+$ independent amino acid transporter and is over-expressed in over-expressed in malignant cell as it plays a critical role in cell growth and proliferation. For functional expression LAT1 requires the heavy chain of the surface antigen 4F2 (heavy chain 4F2hc). The increased accumulation is mainly determined by strongly increased amino acid transport activity rather than incorporation into proteins. A major drawback limiting the applicability of this tracer is however the high renal accumulation.

O-(2-$^{18}$F-ethyl)-tyrosine (FET) and $^{18}$F-alpha-methyl-tyrosine were proposed in 1999 as potential PET tracers. The compounds showed the same uptake properties as IMT. The preparation of these tracers still requires complicated and time consuming synthetic steps and HPLC steps limiting the overall radiochemical yield. They are therefore in practice not very useful.

In the research that led to the invention two new potential SPECT tracers, 2-$^{123}$I-tyrosine (2-$^{123}$I-Tyr) and 2-$^{123}$-I-phenylalanine, were developed. When evaluated in vivo in RIM tumour (rhabdomyo-sarcoma)-bearing rats, these tracers showed high uptake in the tumours (comparable with IMT) while no renal accumulation (10 times less activity in the kidneys than IMT) or high brain uptake was observed. Kinetic studies also revealed that the uptake of radioactive amino acid reflected the amounts of amino acids in the tumour as compared to the blood pool compartment and that no high specific activity is required for the tracer. However, also these tracers are almost limited to SPECT as the positron emitting iodine isotopes $^{124}$I and $^{122}$I do not have the required radionuclide properties for routine patient PET diagnosis.

SUMMARY OF THE INVENTION

It was found that a $^{18}$F-labelled amino acid as tumour tracer shows higher tumour specificity as compared to FDG and is better suited as brain tracer. The fact that within toxicity limits neither high specific activity nor non-carrier added preparation of the $^{18}$F-tracer is required, should allow for electrophilic radio-fluorination making use of [$^{18}$F]-F$_2$. However, the radioisotope production yield with the currently available F$_2$-targets is limited and even with an almost quantitative labelling yield, amounts comparable with those of the $^{18}$F-FDG production are far from being reached and does not allow routine multi patient PET diagnosis.

It is therefore the object of the present invention to provide new compounds and precursors therefor that can be easily and quickly synthesized and can thus also be labelled with F-18 which has a half-life of only 2 hours. It is a further object of the invention to provide the use of such compounds in diagnosis.

The inventors considered based on the results obtained with $^{18}$F-FET and their own results with 2-$^{123}$I-Phe and 2-$^{123}$I-Tyr that the aromatic amino acid properties are conserved after substitution of an O-ethyl group and even in the presence of a voluminous iodine atom. This invention is thus based on the new approach to introduce an alkyl side chain on the phenyl ring to facilitate introduction of the radioactive atom. They thus provided an $^{18}$F-alkyl-phenyl structure in phenylalanine and tyrosine, either ortho, meta or para. Examples are $^{18}$F—CH$_2$—Phe or $^{18}$F—CH$_2$—CH$_2$—Phe and 2-$^{18}$F—CH$_2$—Tyr or 2-$^{18}$F—CH$_2$—CH$_2$—Tyr. This reduces the labelling chemistry to direct conventional nucleophilic aliphatic substitution on the alkylphenylic side branch of the L-amino acid. In this approach cumbersome stereospecific synthesis is not required. The same strategy was followed for the radio-fluorination of the aliphatic amino acids leucine and isoleucine. Preliminary uptake experiments in R1M cells in vitro in a buffer simulating in vivo conditions, showed for $^3$H-leucine and $^3$H-isoleucine results comparable with 3H-Tyr and $^3$H-Phe. Since aliphatic-substituted F hardly changes the pharmacology, it follows that these aliphatic amino acids are also suitable molecules for radio-fluorination.

DETAILED DESCRIPTION OF THE INVENTION

The invention thus relates to halogenated amino acid analogues having the he general formula

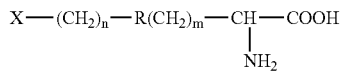

wherein:
R is $(C_1–C_6)$alkyl optionally substituted with thioether or ether oxygen atom when n=0, or a substituted aromatic or heteroaromatic ring when n=1–6; and m=0 or 1; and
X is a halogen atom.

R is preferably an alkyl selected from methyl, ethyl, propyl, isopropyl, butyl, tertiary butyl or methyl thioethyl ether when n is 0 and R is preferably phenyl, hydroxyphenyl, pyridyl, hydroxypyridinyl when n is 1, 2 or 3.

The radioactive halogen atom is preferably a radioactive fluorine, in particular $^{18}$F because of its radionuclidic properties which makes it within the positron emitting isotopes the most interesting for labelling tracer molecules for diagnosis with PET.

Suitable amino acid analogues of the invention are analogues of the aromatic or heteroaromatic amino acids phenylalanine, tyrosine and azatyrosine or the alkyl amino acids alanine, valine, leucine, isoleucine and methionine. The aromatic amino acids are preferably derivatized at the 2 position (phenyl) and 3 position (2-pyridyl analogue) with a $(C_1–C_2)$alkyl methyl and ethyl. The alkyl can also be present at the 3 and 4 position on the aromatic ring of phenylalanine and 5 position in meta-tyrosine.

Preferred analogues are selected from the group consisting of [$^{18}$F] labelled β-2-fluoromethylphenyl-α-aminopropionic acid, [$^{18}$F] labelled β-3-fluoromethylphenyl-α-aminopropionic acid, [$^{18}$F] labelled β-4-fluoromethylphenyl-α-aminopropionic acid, [$^{18}$F] labelled β-2-fluoroethylphenyl-α-aminopropionic acid, [$^{18}$F] labelled β-3-fluoroethylphenyl-α-aminopropionic acid, [$^{18}$F] labelled β-4-fluoroethylphenyl-α-aminopropionic acid, [$^{18}$F] labelled β-2-fluoromethylphenyl-α-aminopropionic acid, [$^{18}$F] labelled β-3-fluoromethyl-2-pyridyl-α-aminopropionic acid, [$^{18}$F] labelled β-4-fluoromethyl-2-pyridyl-α-aminopropionic acid, [$^{18}$F] labelled β-5-fluoromethyl-2-pyridyl-α-aminopropionic acid, [$^{18}$F] labelled β-3-fluoroethyl-2-pyridyl-α-aminopropionic acid, [$^{18}$F] labelled β-4-fluoroethyl-2-pyridyl-α-aminopropionic acid, [$^{18}$F] labelled β-5-fluoroethyl-2-pyridyl-α-aminopropionic acid, [$^{18}$F] labelled 2-amino-3-(5-fluoromethyl-3-hydroxyphenyl)propianoic acid, [$^{18}$F] labelled 2-amino-3-(6-fluoromethyl-3-hydroxyphenyl)propianoic acid, [$^{18}$F] labelled 2-amino-3-(2-fluoromethyl-4-hydroxyphenyl)propianoic acid, [$^{18}$F] labelled 2-amino-3-(2-fluoroethyl-5-hydroxypyridyl)propianoic acid, [$^{18}$F] labelled 2-amino-3-(3-fluoroethyl-5-hydroxy-2-pyridyl)propianoic acid, [$^{18}$F] labelled 2-amino-3-(5-fluoroethyl-3-hydroxyphenyl)propianoic acid, [$^{18}$F] labelled alanine, [$^{18}$F] labelled valine, [$^{18}$F] labelled leucine, [$^{18}$F] labelled isoleucine and [$^{18}$F] labelled methionine. Of these the analogues of which the 2 OR 6 position of the aromatic ring is substituted with the alkyl are found to be preferred because the 4 position (para) is not sterically hampered for biochemical recognition. The invention also relates to all of the above compounds that carry a non-radioactive label, in particular a non-radioactive fluorine atom.

The invention further relates to a pharmaceutical composition comprising one or more amino acid analogues as claimed and an excipient, carrier or diluent. The excipient, diluent or carrier can be any compound or composition in liquid form, that is sterile and non-pyrogenic and can be isotonic saline or an isotonic buffer.

The pharmaceutical composition can be used as a tracer in Positron Emission Tomography (PET) and functional MRI.

The invention further relates to the use of the amino acid analogues in the preparation of a pharmaceutical composition for the diagnosis of cancer.

According to another aspect thereof the invention provides a method for diagnosing a patient for the presence of tumours and/or metastases, which comprises administration of a diagnostic effective amount of one or more of the amino acid analogues, and visualising the localisation of the analogues in the patients body, such as by means of PET, or functional MRI.

The present invention further provides precursor compounds for preparing the amino acid analogues, which precursors have the general formula

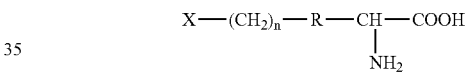

wherein:
R is $(C_1–C_4)$ alkyl when n=0 or phenyl or pyridyl when n=1, 2 or 3;
X is a leaving group, in particular tosyl, mesityl triflate or a halogen; and
NH$_2$ and COOH are protected.

The substitution of an alkyl group, provided with an appropriate leaving group, on the phenyl ring of an aromatic amino acid; such as phenylalanine or tyrosine, or introduction of a leaving group on the aliphatic side chain of alkyl amino acid allows for introduction of the radioactive atom, in particular fluorine, such as $^{18}$F, by aliphatic nucleophilic substitution. This is a quick synthesis step allowing a high radioactive labelling yield.

The COOH may be esterified with a $(C_1–C_5)$alkyl. The $(C_1–C_5)$alkyl is selected from the group consisting of methyl, ethyl, propyl, isopropyl, tertiary butyl, neopentyl. NH$_2$ may be protected with a group selected from N-Boc, N-trityl, f-moc or others. The technology of protecting with these compounds is well known to the person skilled in the art and for example described in Protecting Groups in Organic Synthesis, T. W. Greene, John Wiley & Sons, 1981.

In the precursor compounds R is preferably methyl, ethyl, propyl, isopropyl, isobutyl, 1-methyl butyl, methyl thioethyl ether when n is 0 and R is preferably phenyl, hydroxyphenyl, pyridyl, hydroxypyridyl when n is 1, 2 or 3.

The halogen that may be used as a leaving group in the precursor molecules may be a "cold", i.e non-radioactive halogen.

Suitable precursor compounds of the invention are analogues of the aromatic amino acids phenylalanine and tyrosine, the hetero aromatic azatyrosine or the alkyl amino acids alanine, valine, leucine, isoleucine and methionine. The aromatic amino acids are preferably derivatized at the 2 position (phenyl) or the 3 position (pyridyl) with an ($C_1$–$C_2$) alkyl, such as methyl, ethyl, so that the 4 position (para) is not sterically hindered for biochemical recognition. The alkyl can also be present at the 5 position on the aromatic ring in meta-tyrosine.

The precursor molecules based on alkylated aromatic amino acids can be prepared starting from commercially available alkyl amino acids such as L-2-$CH_3$-Phe. L-2-CH3-Phe will be protected by esterification ($^t$But) and as N-Boc or N-trityl and radicalar mono-bromination or iodination of the 2-methyl group is performed. A tosyl (Tos), mesityl (Mes) or a triflate (Trif) group and any other suitable leaving group is introduced by nucleophilic exchange. After purification, the compound is stored under nitrogen.

As L-/D-2-Br-Phe is commercially available, precursor compounds with Br as the halogen can also be obtained by a Wurtz-Fittig reaction, using dibromomethane and then applying the same pathways as described above.

L-2-Tos(Trif)-$CH_2$-Tyr can be prepared starting from $CH_3$O-L-2-I-Tyr, which is commercially available and is an adequate precursor for the Wurtz-Fittig pathway mentioned above.

For the synthesis of L-/D-2-(Tos, Mes, Trif)ethyl-Phe, L-/D-4-(Tos, Mes, Trif)ethyl-Phe, L-/D-2-(Tos, Mes, Trif) methyl-Tyr and L-/D-2-(Tos, Mes, Trif) ethyl-Tyr, the same strategies are followed.

For Val, Leu and Ile a place specific bromination is applied, followed by introduction of the appropriate leaving group.

The invention further relates to a method for preparing the amino acid analogues of the invention comprising substitution of the leaving group with a radioactive halogen atom. The substitution may take place by means of aliphatic nucleophilic substitution of tosyl, mesityl or triflate with a radioactive halogen, in particular fluorine, or by means of exchange of the halogen leaving group with a radioactive halogen, in particular a radioactive fluoride.

When the aliphatic nucleophilic substitution of tosyl, mesityl or triflate or non-isotopic exchange is used for preparing the radioactively labelled amino acid analogues this will result in a carrier-free preparation, because after substitution the radioactive molecules are separated from the precursors. In case the isotopic exchange method is used a carrier-added preparation is obtained. The specific activity of this preparation depends on the amount of non-radioactive precursor present.

The amino acid analogues and precursor compounds of the invention can have the L and D orientation. The method of the invention for producing the labelled amino acid analogues can use either L or D compounds or mixtures thereof as the starting material thus leading to either L or D analogues or mixtures thereof.

The present invention will be further illustrated in the Examples that follow and that are not intended to limit the invention in any way. Reference is made to the following figures:

FIG. 1: Inhibition of $^3$H-Phe/Phe uptake in R1M cells in vitro by L-2-F-methyl-PHE. The common intercept proves that the inhibition is competitive and that L-2-F-methyl-Phe uses the same transport system as L-Phe.

Figure 2:
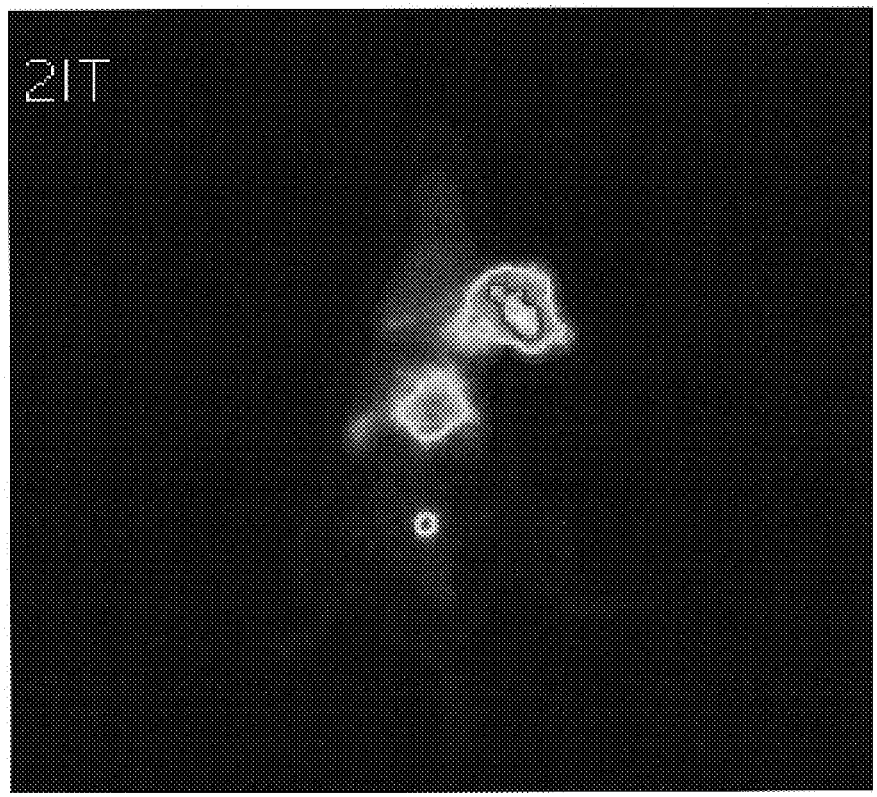

FIG. 2: PET of R1M tumour bearing rat. The tumour is visible at the upper right, the pancreas in the middle and the bladder under. 120 Mbq L-2-$^{18}$F-methyl-phenylalanine was intravenously injected.

EXAMPLES

Example 1

Synthesis of Precursor Molecules and Non-radioactive Fluorinated Analogues 1.1. Protected L-2-bromomethyl-PHE On L-2-methyl-Phe the tributyl ester and N-Boc protection is introduced by conventional chemistry (N-Boc: (BOC)$_2$O, TEA, MeOH/tButOH, room temperature, 2 hours; Butylester: TMSL+tButOH or Li—O-t-butyl, room temperature, 24 hours). The protected compound is reacted in $CCl_4$ with Br-succinimide in the presence of benzoylperoxide as catalyst (radical halogenation) at 80° C. during 1 hour. After precipitation of the succinimide the product is purified by column chromatography.

As alternative for benzoylperoxide an irradiated polymer like PMMA is used as radical promotor, this allows the purification by simple filtration.

1.2. Protected L-2-Tosethyl-Phe

L-2-I-Phe is obtained by $Cu^{1+}$ assisted iodo for bromo exchange on commercial available L-2-Br-Phe in acidic reducing aqueous condition (gentisic acid and $SnSO_4$ as reducing agent for $CuSO_4$). Protection is introduced as in 1.1. The ethyltosyl is introduced in 3 steps (a: vinylbromide, Pd(PPh$_3$)$_4$, 1,4-dioxane, 100° C., 1 hour; b: BH$_3$-THF complex, 4N NaOH, 30% $H_2O_2$, THF, 0° C., 2 hours; c: TsCl, DMAP, $CH_2Cl_2$, room temperature, 2 hours).

1.3. Protected brominated Leucine

Protection is performed as described in 1.1. and 1.2. Radical bromination is performed as described in 1.1.

1.4. Protected L-2-alkyltosyl-Tyrosine

L-2-I-Tyr is commercially available. The chemistry is the same as described for L-2-I-phenylalanine in 1.2.

1.5. Protected bromoleucine

N-Boc, t-Butyl protected leucine is brominated by a radical reaction as described in 1.1.

1.6. Non radioactive fluorinated analogues

These are obtained by reaction at reflux temperature of the Tosylated precursor molecules with nBu$_4$NF in $CH_3CN$.

Example 2

Radiochemical Synthesis of Compounds of the Invention

L-D-$^{18}$F-R-Phe analogues (R=methyl or ethyl) are prepared by nucleophilic exchange of $^{18}$F on L-/D-2-TosR-Phe in an AcN/TBA/HCO$_3^-$ or AcN/K$_{222}$/CO$_3^{2-}$ mixture at 85° C. during 5 minutes.

In short, $^{18}$F$^-$ is separated from the target water via an anion exchange column. Elution of the activity is achieved with tetra-n-butyl ammonium hydrogen carbonate in $H_2O$. $H_2O$ is discarded by azeotropic distillation after addition of acetonitrile. L-2-Tosethyl-N-trityl-phenylalanine tert. butylester in dry acetonitrile is added to the $^{18}$F$^-$ recipient and heated during 3–5 minutes at 85° C. After the reaction the solvent is evaporated by means of pre-heated N$_2$.

Then, two pathways are possible. First, de-esterification and de-protection are preformed in solution followed by HPLC or mini-column purification. Alternatively, straightforward de-protection can be performed on a mini-column followed by HPLC or another type mini-column purification.

For L-/D-$^{18}$F-Leu and L-/D-$^{18}$F-Ile an analogous radiochemistry is applied.

Example 3

In Vitro Affinity for Cancer Cells

The affinity of L-2-F-methyl-phenylalanine for uptake by the L-transport system 1 (LAT1) in cancer cells (rat rhabdomyo-sarcoma cells) was determined by measuring the inhibition of the uptake of L-$^{3}$H-phenylalanine after 15 minutes incubation in HEPES buffer of pH 7.4 containing appropriate amounts of L-phenylalanine and of L-2-F-methyl-phenylalanine. The uptake was saturable and followed the typical Michaelis-Menten relation allowing to draw Lineweaver-Burk (FIG. 1) plots.

The double reciprocal plots in FIG. 1 with a common intercept almost on the 1/uptake axis shows that the inhibition is competitive with the phenylalanine uptake and uses the same LAT transporter system.

A mean $K_i$ value of 76 μM was obtained for L-2-F-methyl-phenylalanine. This value is almost comparable with the $K_m$ value of 65 μM obtained for the natural L-phenylalanine in the same conditions.

Example 4

In Vivo Rat Evaluation of L-2-18F-methyl-phenylalanine in a R1M Tumour Bearing Rat by Means of PET FIG. 2 shows that high uptake is observed in the tumour and pancreas. The latter is typical for rodent. It shows that the $^{18}$F-methyl-phenylalanine analogue is transported as a natural amino acid. No accumulation in the kidneys or other organs is observed. The product is cleared through the kidneys to the bladder.

I claim:

1. A halogenated amino acid compound of formula:

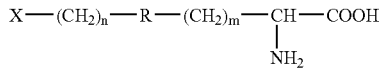

wherein:
X is a radioactive halogen;
m is 0 or 1,
n is 1, 2, 3, 4, 5, or 6;
R is an aromatic ring, a heteroaromatic ring, or a substituted aromatic or heteroaromatic ring; and the X—(CH$_2$)$_n$— is a side chain on the ring.

2. A halogenated amino acid compound of formula:

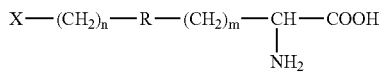

wherein:
X is a radioactive halogen;
m is 0 or 1;
n is 1, 2, 3, 4, 5, or 6; and
R is phenyl having the X-(CH$_2$)$_n$- as a side chain, hydroxyphenyl, pyridyl, or hydroxypyridyl.

3. The compound of claim 1, wherein the halogen is $^{18}$F.

4. The compound of claim 1, wherein the halogen is $^{123}$I.

5. The compound of claim 1, wherein the analogue is selected from the group consisting of: [$^{18}$F] labeled L,D-2-amino-3-(2-fluoromethyl-phenyl)-propionic acid; [$^{18}$F] labeled L,D-2-amino-3-(3-fluoromethyl-phenyl)-propionic acid; [$^{18}$F] labeled L,D-2-amino-3-(4-fluoromethyl-phenyl)-propionic acid; [$^{18}$F] labeled L,D-2-amino-3-(2-fluoroethyl-phenyl)-propionic acid; [$^{18}$F] labeled L,D-2-amino-3-(3-fluoroethyl-phenyl)-propionic acid; [$^{18}$F] labeled L,D-2-amino-3-(4-fluoroethyl-phenyl) propionic acid; [$^{18}$F] labeled L,D-2-amino-3-(3-fluoromethyl-pyridin-2-yl)-propionic acid; [$^{18}$F] labeled L,D-2-amino-3-(4-fluoromethyl-pyridin-2-yl)-propionic acid; [$^{18}$F] labeled L,D-2-amino-3-(5-fluoromethyl-pyridin-2-yl)-propionic acid; [$^{18}$F] labeled L,D-2-amino-3-(6-fluoromethyl-pyridin-2-yl) propionic acid; [$^{18}$F] labeled L,D-2-amino-3-(3-fluoroethyl-pyridin-2-yl)-propionic acid; [$^{18}$F] labeled L,D-2-amino-3-(4-fluoroethyl-pyridin-2-yl)-propionic acid; [$^{18}$F] labeled L,D-2-amino-3-(5-fluoroethyl-pyridin-2-yl)-propionic acid; [$^{18}$F] labeled L,D-2-amino-3-(6-fluoroethyl-pyridin-2-yl)-propionic acid; [$^{18}$F] labeled L,D-2-amino-3-(2-fluoromethyl-4-hydroxy-phenyl)-propionic acid; [$^{18}$F] labeled L,D-2-amino-3-(5-fluoromethyl-3-hydroxy-phenyl)-propionic acid; [$^{18}$F] labeled L,D-2-amino-3-(6-fluoromethyl-3-hydroxy-phenyl)-propionic acid; [$^{18}$F] labeled L,D-2-amino-3-(2-fluoroethyl-4-hydroxy-phenyl)-propionic acid; [$^{8}$F] labeled L,D-2-amino-3-(5-fluoroethyl-3-hydroxy-phenyl)-propionic acid; [$^{18}$F] labeled L,D-2-amino-3-(6-fluoroethyl-3-hydroxy-phenyl)-propionic acid; [$^{18}$F] labeled L,D-2-amino-3-(3-fluoromethyl-5-hydroxy-pyridin-2-yl)-propionic acid; [$^{18}$F] labeled L,D-2-amino-3-(3-fluoroethyl-5-hydroxy-pyridin-2-yl)-propionic acid; [$^{18}$F] labeled L,D-2-amino-3-(3-fluoromethyl-6-hydroxy-pyridin-2-yl)-propionic acid; [$^{18}$F] labeled L,D-2-amino-3-(4-fluoromethyl-6-hydroxy-pyridin-2-yl)-propionic acid; [$^{18}$F] labeled L,D-2-amino-3-(3-fluoroethyl-6-hydroxy-pyridin-2-yl)-propionic acid; [$^{18}$F] labeled L,D-2-amino-3-(4-fluoroethyl-6-hydroxy-pyridin-2-yl)-propionic acid.

6. A pharmaceutical composition comprising the compound of claim 1 and at least one of an excipient, carrier and diluent.

7. The pharmaceutical composition of claim 6, wherein the pharmaceutical composition is used as a tracer in at least one of Positron Emission Tomography (PET) and functional Magnetic Resonance Imaging (MRI).

8. A method for preparing the compound of claim 1, the method comprising:
providing a precursor having the general formula

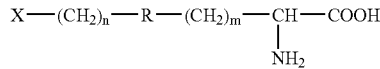

wherein:
X is a leaving group selected from the group consisting of tosyl, mesityl, triflate and a halogen; and
NH$_2$ and COOH are protected; and
substituting a radioactive halogen for the leaving group of the precursor.

9. The method of claim 8 wherein the substitution comprises aliphatic nucleophilic substitution of tosyl, mesityl, or triflate with radioactive fluorine.

10. The method of claim 8 wherein the leaving group is a halogen, and the substitution comprises exchange of the leaving group with radioactive fluorine.

* * * * *